United States Patent
Cerbone et al.

(10) Patent No.: US 8,429,034 B2
(45) Date of Patent: Apr. 23, 2013

(54) INVENTORY CONTROL OVER PHARMACEUTICAL SAMPLE DISTRIBUTIONS SOFTWARE, SYSTEMS AND METHODOLOGIES

(75) Inventors: Kimberly Cerbone, Stamford, CT (US); Balaji Chellappa, Stamford, CT (US); Jay Katira, Norwalk, CT (US); Jake Stahl, Milford, CT (US)

(73) Assignee: Purdue Pharma L.P., Stamford, CT (US)

( * ) Notice: Subject to any disclaimer, the term of this patent is extended or adjusted under 35 U.S.C. 154(b) by 1119 days.

(21) Appl. No.: 11/925,405

(22) Filed: Oct. 26, 2007

(65) Prior Publication Data

US 2008/0103821 A1 May 1, 2008

Related U.S. Application Data

(60) Provisional application No. 60/867,903, filed on Nov. 30, 2006, provisional application No. 60/863,243, filed on Oct. 27, 2006.

(51) Int. Cl.
*G06Q 40/00* (2012.01)
(52) U.S. Cl.
USPC ............................................. 705/28
(58) Field of Classification Search ............... 707/104.1; 705/3
See application file for complete search history.

(56) References Cited

U.S. PATENT DOCUMENTS

| | | | |
|---|---|---|---|
| 6,493,724 B1 * | 12/2002 | Cusack et al. ...................... 1/1 |
| 6,952,681 B2 | 10/2005 | McQuade et al. |
| 2002/0055856 A1 * | 5/2002 | Adams .............................. 705/2 |
| 2002/0161607 A1 * | 10/2002 | Subich .............................. 705/3 |
| 2003/0088442 A1 | 5/2003 | Michael et al. |

OTHER PUBLICATIONS

U.S. Appl. No. 11/925,552, Mietek Ciszkowski, et al.
U.S. Appl. No. 11/925,403, Ciszkowski et al.
U.S. Appl. No. 11/925,491, Arora et al.

* cited by examiner

*Primary Examiner* — Shay S Glass
(74) *Attorney, Agent, or Firm* — Leason Ellis LLP

(57) ABSTRACT

Methods for managing the distribution of samples in support of activities of field representatives which differentiate on-hand and in-storage inventories of samples that have been previously allocated from a master inventory, for example, from the inventory of a pharmaceutical company. Field representatives are assisted in managing an inventory of samples known to a database through an interface including one or more charts or tables that distinguish an on-hand quantity from an in-storage quantity, and a mechanism to identify a quantity of a particular product in the chart or table for distribution, with the database being updated to track changes at least in the on-hand quantity information. The interface can be further configured to capture the signature of a sample recipient over that person's name, presented in a signature block as a watermark in a cursive-font to deter unauthorized sample acceptance.

22 Claims, 5 Drawing Sheets

Fig. 5

| Home | Lists | Calls | Customer ←510 | Promo. Order | Reports |

| Day View | Week View | Calendar | 520→ Call | Meeting | Time Off | Itinerary/Schedule |

[Cancel] [Apply]

- Location [Lisa    Reno,NV ▼] No Best Time for Friday : Click to Add
- Start Date Time [05/31/2006] 📅 [8:00 AM ▼] End Time [8:30 PM ▼]
- Call Type [Presentation ▼]

Accompanied By [-Select Rep/DM/RM- ▼]    Tamper Prf. Script Pad # [_____]

Sample Drop [-Select- ▼] ← 530

Status [Open ▼]                                       500

YTD Amount Spent: $0

Representative Info
Representative Name Joseph
Employee ID ABC123
Geography XYZ01

Customer Detail
Prof. Des. PA
Name: Lisa
Location [Reno NV-89511 ▼]
IMS Number: ABC
ME Number: DEF

⎫
⎬ 610
⎭

State License Number Details

| Licensing State | State License NO | License Expiration Date |
|---|---|---|
| NV | PA529 | 06/30/2007 |

⎫ 620

Select Product for Sampling

|  | Product | Lot Number | Uom | Quantity |
|---|---|---|---|---|
| 💊 | 200mg | 100001 | PACKS | 5 ▼ (75) |
| 💊 | 100mg | 500005 | PACKS | 3 ▼ (75) |
| 💊 | 80mg | 600001 | PACKS | 0 ▼ (13) |
| 💊 | 40mg | 654546464 | PACKS | 0 ▼ (360) |
| 💊 | 20mg | 7656 | PACKS | 0 ▼ (180) |

⎫ 640

[Get Signature] [Cancel]

Sampling History

|  | Product | Lot Number | Quantity | Date ▼ |
|---|---|---|---|---|
| 💊 | 200mg | 100001 | 20 | 6/5/05 |
| 💊 | 100mg | 500005 | 10 | 6/5/05 |

⎫ 630

INVENTORY CONTROL OVER PHARMACEUTICAL SAMPLE DISTRIBUTIONS SOFTWARE, SYSTEMS AND METHODOLOGIES

This patent application claims the benefit of priority under 35 U.S.C. §119(e) of U.S. Provisional Application Ser. No. 60/867,903, filed on Nov. 30, 2006, entitled "Inventory Control over Pharmaceutical Sample Distributions, Software, Systems and Methodologies," and of U.S. Provisional Application Ser. No. 60/863,243, filed Oct. 27, 2006, entitled "Territory Management System," which are hereby incorporated by reference in their respective entireties.

FIELD OF THE INVENTION

The present invention relates to the tools for managing information relating to the activities of field representatives of manufacturers and service providers, and, more particularly, to software, systems and methodologies that assist in the management of sample distribution and inventory.

BACKGROUND OF THE INVENTION

In many sectors, field representatives are used to educate customers and potential customers on the products of manufacturers and service providers. In the course of their duties, sales representatives make site visits and build a relationship with the customers and potential customers in their assigned territory. The field representative may wish to provide samples of his or her products to customers and potential customers. U.S. Published Application No. 2003-0088442 A1 describes a system that divide an inventory kept by a company (e.g., a pharmaceuticals company) so as to have a sub-inventory associated with a particular representative, yet the focus of this and other systems is sample-tracking as between the manufacturer and the representative; there are few tools to assist in the representative in conducting his or her duties. For example, in order to manage the samples allocated to a particular representative, the representative must have such samples with him or her during a site visit in order to distribute them.

Further, in some sectors, a representative may need to limit sample distribution in accordance with various laws, rules, or guidelines. In the pharmaceutical sector, for example, a given health care provider (HCP) may lack state or federal approvals to receive samples, due to expired or not-yet-granted licenses, historical sample distributions, or other reasons. One system described in U.S. Pat. No. 6,952,681 has real-time communications to control distributions to only authorized physicians, yet there are deficiencies in that system including reliance on communications to a central facility and no locally-generated mechanism to deter unauthorized sample acceptance.

The present invention provides software based tools that improve upon the software, systems, and methods available to representatives today.

SUMMARY OF THE INVENTION

In accordance with one aspect of the invention, a method for assisting a representative in managing the distribution of samples to a customer is provided in which the samples to be distributed have been allocated to the representative from a central inventory of a pharmaceutical company. Inventory information is stored in a database of a machine in a form suitable for differentiating among the samples allocated to the representative an on-hand quantity from an in-storage quantity. A user interface of the machine presents a chart or table which distinguishes the on-hand quantity from an in-storage quantity of at least one product. An identification of a product included in the chart or table and a quantity of the product is received from the representative. The database is updated so as to track at least changes in the on-hand quantity information concerning the product stored in response to the receiving step. The database update is communicated to a central machine which differs from the machine.

In another aspect of the invention, there is again a method for assisting a representative in managing the distribution of samples to a customer is provided in which the samples to be distributed have been allocated to the representative from a central inventory of a pharmaceutical company. In accordance with this aspect of the invention, the method includes the steps of selecting the customer from a database included on a machine, populating a sample selection table using quantity information stored in the machine for each of one or more products, receiving a quantity selection concerning the one or more products in the populated sample selection table, and outputting an acceptance form having a signature region configured to receive the customer signature. The acceptance form identifies the representative, the selected customer, and the received quantity selection for each of the one or more products. In addition, the acceptance form includes a watermark comprising the customer name in a cursive font within the signature region. In a further, optional aspect, the method can further include rules which are utilized to influence the determination as to which product samples are to be presented in the sample selection table, such as whether the selected customer can be provided particular product samples.

Also provided are inventory management tools that can use one or more of the foregoing methods in connection with inventory changes as a result of an inventory adjustment, a return of the sample to a manufacturer, an inventory transfer step with another representative, or a physical inventory audit.

These and other aspects, features, and advantages will be apparent from the following description of certain embodiments and the accompanying drawing figures.

DESCRIPTION OF THE DRAWING FIGURES

FIG. 5 is a sample customer summary form which can be used to launch a sample drop request;

FIG. 6 is a sample form for selecting samples to distribute, as may be used in connection with the flow diagram of FIG. 4.

DETAILED DESCRIPTION OF CERTAIN EMBODIMENTS

Figure 1:
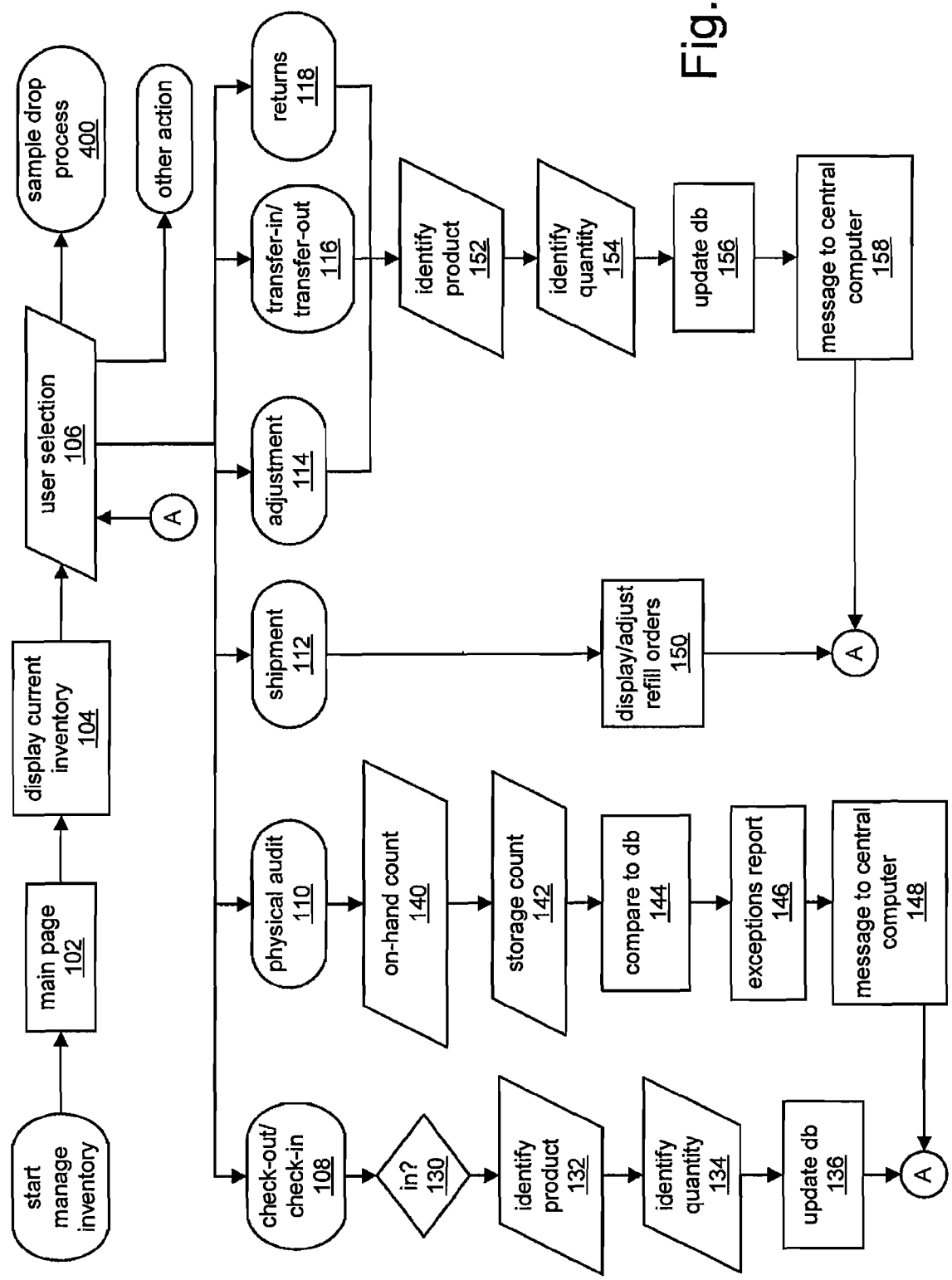
FIG. 1 is a flow diagram illustrating a menu of inventory management tools available for selection by a field representative, as may be part of a multifunction territory management software application.

By way of overview and introduction, a territory management system provides representatives with a tool for conducting their activities in an efficient manner, and in relevant part includes functionality adapted to assist a field representative in managing an inventory of samples allocated to him or her, including selective distribution to persons within his or her territory.

The management system is preferably implemented as a software-based system, having components executing on a number of systems including a central computer and a multiplicity of remote machines, with each representative having a remote machine for his or her personal use. Without loss of generality, the present invention is described in relation to a particular representative using a single remote machine in the course of his or her activities covering an assigned territory. While the described embodiment has the inventory database and customer information stored on a machine used by the representative, it can be stored on different machines, such as the central computer or on a workstation component that cooperates with a comparatively thin client with which the representative interacts. In the preferred embodiment described below, the representative is bespoke or contracted to a pharmaceutical manufacturer, and the representative "covers" a territory through visits to health care providers ("HCPs"), physicians and nurses (collectively, more generally, "prescribers") at which the representative is able to discuss and promote the use of the manufacturer's products. However, the invention has industrial applicability in other many sectors including in connection with field representative activities in promoting products and services of general nature, including, without limitation, in the personal care, medical device, toy, consumer electronics, office equipment, and construction equipment sectors.

A preferred software tool for territory management is described, in part, in the aforementioned U.S. Provisional Application Ser. No. 60/863,243, entitled "Territory Management System." The Territory Management System software provides through a Web-browser interface a number of tools that assist the representative in planning, recording, and tracking activities with customers such as prescribers. In relevant part, the Territory Management System software can assist a representative with managing, processing and deciphering sales information following their efforts in servicing his or her assigned territory. The Territory Management System software includes additional features that can assist representatives in other ways, such as in complying with concerning certain regulatory requirements or state or federal constraints concerning expenses incurred in connection with visiting with health care professionals, reporting adverse events, in scheduling site visits to HCPs, and in gauging the effectiveness of the messages that they are trying to deliver. Various features of the Territory Management System software are described in certain co-pending provisional patent applications which are referenced below to the extent they have pertinence to the discussion of the present invention.

The remote machine used by the representative includes a suitable complement of hardware and software including, by way of example, a processor, memory, an accessible database, communications equipment, and input/output devices.

Figure 2:
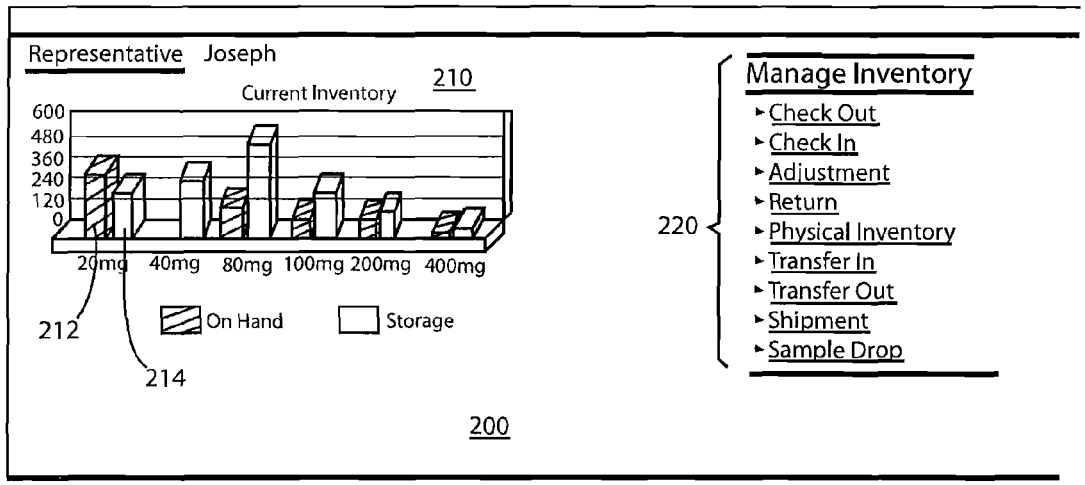
FIG. 2 shows a sample inventory chart and a selection menu of functions that can be launched from a main page, including the functions depicted in FIG. 1.

Referring now to FIGS. 1 and 2, a set of inventory management tools are provided on the representative's machine through a user interface which includes a main page 200. The main page can be accessed in a number of ways during the course of using the territorial management system, including by selecting an appropriate tab, button or other control. At block 102, the main page 200 is displayed. At block 104, as part of the main page, a chart 210 of the current inventory of samples that have been allocated to the representative, e.g., by the manufacturer, is displayed. Instead of a chart (which term includes a graph or other graphical depiction of information), the inventory information can be included in a table. The current inventory of samples as understood by the system as being in the possession of the representative has two components for each product that the representative represents: on-hand inventory 212 and in-storage inventory 214. This distinction is made within the user interface because the representative can have more samples assigned to him at a given moment in time (that is, allocated to him) than might be appropriate to have on-hand while traveling to meet customers. Thus, the current inventory chart 210 has for each of six products, two bar graphs, one for on-hand inventory 212 and in-storage inventory 214. Meanwhile, the database can store the inventory information in a number of ways to permit this distinction to be displayed. For example, the on-hand and in-storage inventory quantities can be separately stored tallies of inventory for each product. Alternatively, the total quantity of each product can be stored as well as either the on-hand or in-storage subtotals, from which the other can be determined.

The main page also has user selectable menu options 220 which can be used to launch various inventory management functions. The options are selectable through the interface, such as by a click-selection with a pointer device, and are obtained by the software at block 106. Depending on the user selection, different processes can be launched. The various processes that can be launched can be implemented in tandem with other functions, such as a download or upload operation which may be engaging some of the representative's machine's resources.

By way of overview, a number of inventory management functions can be launched, including the sample-drop process 400 of the present invention (discussed in detail below), a check-out/check-in process 108, a physical audit process 110, a shipment management process 112, an inventory adjustment process 114, a transfer-in/transfer out process 116, a returns management process 118, or some other process (for example, an unrelated function that has been selected through the user interface). An overview of these collateral processes is described followed by a discussion of the sample-drop process.

The check-in/check-out process 108 is a management function useable by the representative to record on a daily basis, if desired, the movement of the samples that have been allocated to him or her from a master inventory, such as the central inventory of a pharmaceutical company. In particular, this process can manage the movement of samples from in-storage inventory 214 to on-hand inventory ("check-out") and the movement of samples from on-hand inventory back to in-storage inventory 214 ("check-in"). The process flow generally includes determining whether this is a check-in or check-out process, as indicated at block 130, and then proceeding with the same basic steps. It is helpful to consider one instance or the other, and so the following description will concern steps taken to check-in samples that were previously checked out. At block 132, the product being checked-in is identified. This product will be selectable from a list, preferably, a list of samples known to have been checked-out, and, more preferably, from a list of samples known to be checked-out and further believed to not have been distributed. At block 134, the quantity of the samples of the identified product being checked-in is input. The local database of the representative's machine is updated, as indicated at block 136, to reflect this change in status. The process flow can then loop back to obtain a further selection, as indicated by the terminator "A."

With regard to the check-out process, the steps are the same except that the product being checked-out, which is identified at block 132, preferably is selectable from a list of samples known to be in in-storage inventory.

The physical audit process 110 is a management function useable by the representative to confirm an actual count of inventory of samples assigned to the representative, that is, the inventory of samples allocated to that representative from a master inventory, as described above. Optionally, the territory management software can provide alerts to the representative to initiate a physical audit if the system determines that this function has not been utilized for a day, week or other period of time. At block 140, the representative provides a manual input of the on-hand inventory 212 count for a particular product. At block 142, the representative provides a manual input of the in-storage inventory 214 count for that same product. The input data is compared to the state of the local database on the representative's machine, at block 144, and if there is any discrepancy, it is noted in an exceptions report, as indicated at block 146. Optionally, the issuance of an exceptions report can cause a message to be composed for sending to the central computer the next time that the representative's machine is in communication with the central computer over a suitable communication link. The message can be transmitted and other data exchanged between the two machines in accordance with co-pending U.S. Provisional Application Ser. No. 60/867,943, filed on Nov. 30, 2006, entitled "Data Cache Techniques In Support Of Synchronization of Databases In A Distributed Environment," which is hereby incorporated by reference in its entirety. Once, again, the process flow can then loop back to obtain a further selection, as indicated by the terminator "A."

Figure 3:
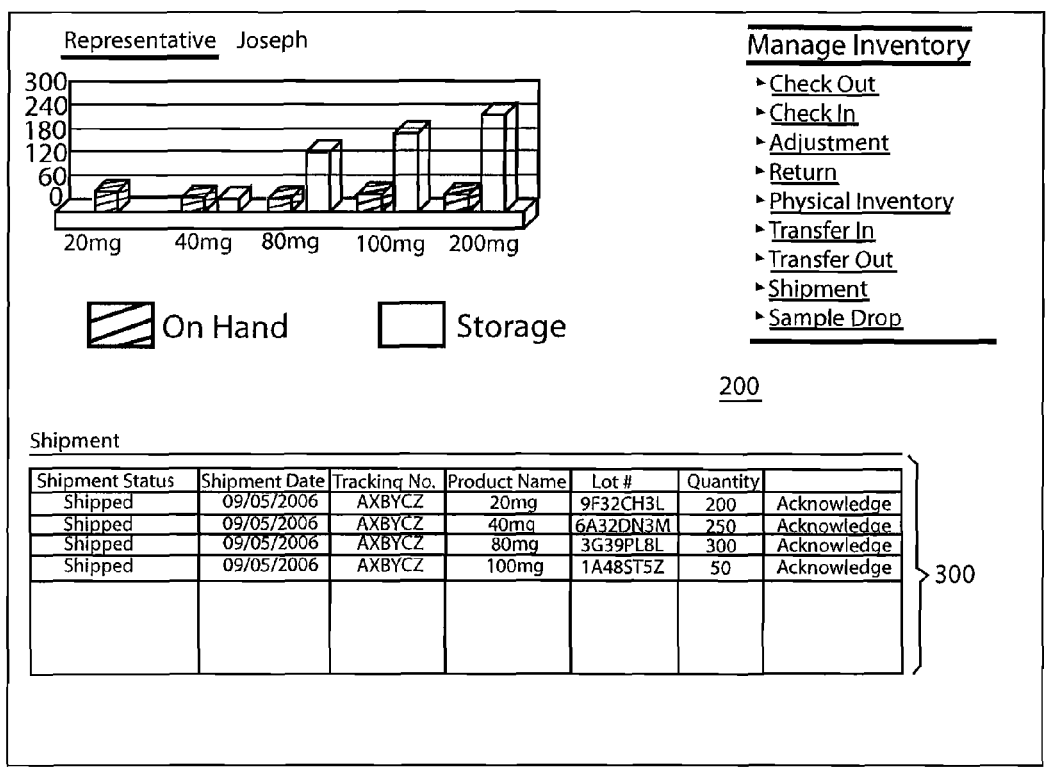
FIG. 3 is a sample form useful in connection with managing shipment orders that refill or add samples to the representative's inventory.

The sample shipment process 112 is a management function useable by the representative to display, adjust, and acknowledge refill orders or new sample orders, as indicated at block 150. As shown in FIG. 3, an interactive table 300 includes relevant sample shipment data, including shipment status (ordered, out of stock, shipped), its shipment date, if applicable, a tracking number, if any, a product name, a lot number, a quantity of the shipment order, and a field to acknowledge/mark acknowledged the order. This information is pulled from the local database of the representative's machine, as may be updated from time to time during the course of an upload/download session with the central computer, and can be displayed directly within the main page 200 (as shown), or on a separate page. When the user interface is provided through a Web browser, as is presently preferred, the database access call that presents the interactive table can be performed using an Asynchronous JAVAScript and XML command (AJAX), which allows further data to be retrieved from the local database and displayed in the current page 200 without reloading the entire page, and without requiring a connection to the central computer. The process flow can then loop back to obtain a further selection, as indicated by the terminator "A." When a different inventory function is selected, the portion of the page 200 including the table 300 can be refreshed with different information.

The sample adjustment process 114 is a management function useable by the representative to correct the inventory records in the unlikely event of a mismatch between total samples in possession of the representative (on-hand and in-storage) and the total stored in the database, namely, that representative's total allocation of samples not-yet-distributed. In the case of a mismatch, the product is identified (block 152), the unaccounted for quantity is input (block 154), the database is updated (block 156), and a message is sent to the central computer (block 158). These actions are not substantially different in character than previously described in connection with blocks 132, 134, 136, and 148, respectively. The process flow can then loop back to obtain a further selection, as indicated by the terminator "A."

The transfer-in/transfer-out process 116 is a management function useable by the representative to transfer samples in from another representative or out to another representative. As such, this functionality provides a mechanism for the representative to account for movement of his or her inventory (that is, allocation) locally, using this feature of the territory management system. The steps taken for transferring-in or transferring-out samples generally follow those described previously, and include: identifying the product being transferred (block 152), inputting the quantity being transferred (block 154), updating the database (block 156), and informing the central computer of this movement of samples (block 158). A corresponding process is expected to occur on the machine of the other party to the transfer process. A manager can monitor the net movement and ensure that the transferred samples allocated to both representatives are accounted for properly.

The returns process 118 is a management function useable by the representative to send samples back to the manufacturer and thereby reduce the net allocation of samples to that representative. The steps taken are substantially the same as performed in connection with the adjustments and transfer processes, and are not discussed further herein.

Figure 4:
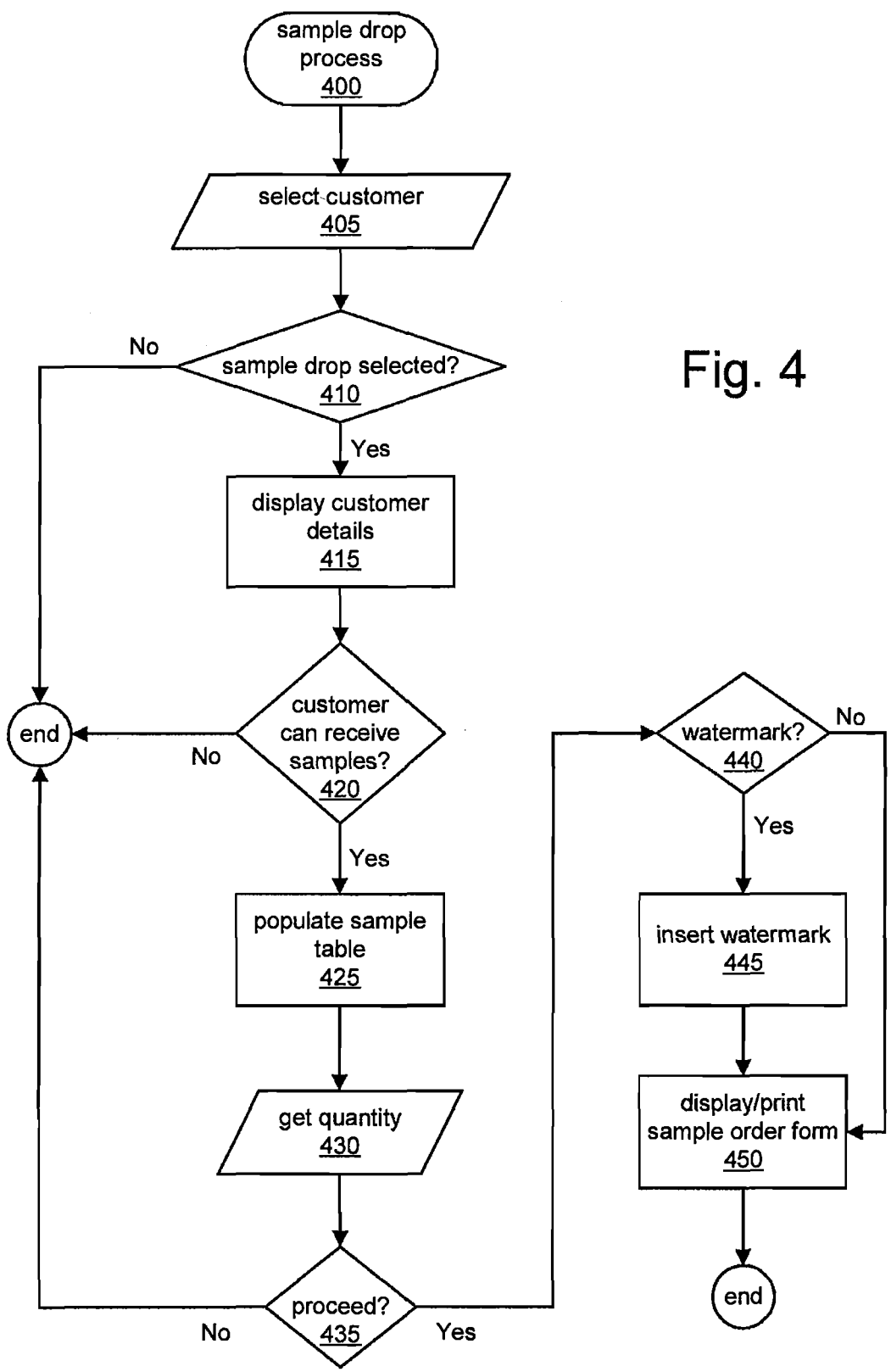
FIG. 4 is a flow diagram illustrating a sample distribution method in accordance with an embodiment of the invention.

Reference is now made to the embodiment of a sample drop process shown in FIG. 4, which, in accordance with a salient aspect of the invention, can be used by the representative to manage the distribution of samples from on-hand inventory to a HCP who is authorized to receive such samples. At block 405, the sample-drop method starts with the representative interacting with this feature of the territory management software by selecting a customer. A customer can be selected in a variety of ways, including from a customer call page 500, as shown in FIG. 5. The customer call page is accessed by selecting a customer tab 510, and a call tab 520.

The customer call page and the various manners of selecting a customer (e.g., by interacting with various tabs, buttons, or other controls provided through the territory management system user interface) are more fully described in U.S. Provisional Application Ser. No. 60/867,923, filed on Nov. 30, 2006, entitled "Adverse Event Data Capture Software, Systems, And Methodologies" ("AE Capture"), U.S. Provisional Application Ser. No. 60/867,906, filed Nov. 30, 2006, entitled "Pharmaceutical Representative Expense Report Management Software, Systems, And Methodologies," U.S. Provisional Application Ser. No. 60/868,015, filed on Nov. 30, 2006, entitled "Cycle Planning Tool for Territory Management" and U.S. Provisional Application Ser. No. 60/868,027, filed on Nov. 30, 2006, entitled "Itinerary Search Tool for Territory Management," which are each hereby incorporated by reference in their respective entireties.

At block 410, a test is made to determine whether the sample-drop functionality has been selected. Whether a particular customer can receive samples preferably is part of a test made prior to displaying information regarding any particular customer or set of customers. In the event that sample drop is permitted, for example, because the customer has prescription-writing privileges and a valid, unexpired license to do so, then controls can be provided in association with the customer to permit the sample drop functionality to be initiated. For example, an interactive icon such as a picture of a pill can be displayed together with the customer's name (in a table or with a summary data record concerning the customer). Selection of the control also can be made from a main page provided for this purpose. In either case, selection of the control initiates the sample-drop process. In the form 500, a pull-down list 530 enables the representative to confirm that distribution of a sample to that prescriber has occurred.

If the sample-drop function is not selected, the process flow ends. On the other hand, if sample-drop has been selected, then details regarding the selected customer are presented to the representative, as indicated at block 415 and as shown in FIG. 6. The details displayed to the representative, in the sample form of FIG. 6, include region 610 which has the representative's details (name, employee ID, territory/geographic region) and the physician's name, location, IMS and ME numbers, region 620 which has the physician's state license details including license expiration date, and the sampling history 630—a table showing the products, lot numbers, quantities, and dates on which samples were previously provided to that physician. In the event of a recall of a particular lot, the sampling history can be searched to identify the distribution of samples that are subject to recall and to initiate the recall process. The sampling history is augmented each time a customer accepts the distribution of samples, such as by signifying acceptance on the form 700, discussed below. The sampling history is stored as distribution data, preferably in association with the lot number of each sample. In this way, if a particular lot number is subject to a manufacturer recall, any distribution from the representative's inventory can be matched to the particular customer to whom it was distributed, and a recall message can be communicated to the customer, or the representative, or both, to better ensure that all samples are recalled. Likewise, samples that remain within the representative's inventory can be matched with recall lot numbers to better ensure that those samples (whether on-hand or in storage) are not distributed after the recall message is communicated.

At block 420, a test is made to determine whether the selected customer can receive samples. This test is preferably performed as a background process before displaying the sample form 600, and more preferably precedes the presentation of any control that permits the sample-drop process to be initiated by the user. For example, control can be selectively presented after performing a threshold test to determine whether a particular customer can receive samples (e.g., is a prescriber, has an unexpired license, etc.), and then displaying the control either a main page provided for this purpose or in association with a customer (e.g., as a pill icon symbolizing that sample-drop is permitted). If the selected customer is not indicated as being able to receive samples, then the sample selection table 640 need not be populated with any products, and the process ends awaiting further action by the representative. For example, a family medicine doctor may be indicated to receive certain samples, but not to receive other samples that are for doctors in a different practice category. Also, if a license has expired or not yet been granted, that could be a basis for disqualifying the HCP from receiving one or more samples during the site visit. If the selected customer is indicated as being able to receive certain samples, but not others, then the sample selection table 640 can be populated accordingly, as indicated at block 425. It should be understood that a sample could have an expiration date which causes it to not be selectable, rather than the causing residing with the selected customer. Also, the sampling history 630 information can provide a basis for not distributing further samples of a given product at the time of the site visit. In any event, the sample selection table 640 can be populated with all of the samples that the representative has to distribute that are appropriate for distribution to the selected customer. Optionally, the sample selection table 640 registers quantities of each product as a function of the local database count of samples on-hand, or total count of samples on-hand and in-storage. If there are no samples of a particular product on-hand (or in-storage), the sample can be shown in the table with a zero quantity, or can be omitted from the sample selection table.

At block 430, the representative interacts with the sample selection table 640 to indicate a quantity of each drug product to be distributed to the selected physician. Once the representative has finished adjusting the quantities, he can proceed or cancel the transaction.

At block 435, a test is made whether the representative has indicated that he or she wishes to proceed. The test can be an event-driven test, such as click-selecting a "proceed" button to prepare a transaction form suitable for the proposed sample distribution to this customer. Similarly, the test at block 435 can respond to a "cancel" operation by terminating this process flow, and returning the representative to the main page 200 (or elsewhere).

Figure 7:
FIG. 7 is a sample transaction form for securely distributing samples to customers, as may be used in connection with the flow diagram of FIG. 4.

If the representative elects to proceed, a sample transaction form 700 can be displayed through the interface, as shown in FIG. 7. The sample transaction form 700 includes information sufficient to track the distribution of samples from a particular representative to a specific physician, including details on the samples themselves to permit recall, if necessary. Information identifying the representative is included in region 710, such as the representative's name, employee identification number, and the territory to which he or she is assigned. The details of the customer to whom samples are to be distributed are included in region 720, such as the physician's name, address, IMS and ME numbers, state license number, and the sample drop date. A product list 730 is preferably a tailored list which reflects the actual selections made in the sample selection table 640. The sample transaction form 700 includes a signature section 740 which includes boilerplate language confirming that the physician is a licensed practitioner and has requested the package quantities of the products identified in the product list 730. The signature section includes a signature block 750.

Preferably, as conceptually shown as a test at block 440, a decision is made as to whether to include a watermark 752 within the signature block. The decision as to whether to include a watermark can be a configuration setting that governs all of the sample transaction forms 700, or the decision can be made each time the form is presented.

A watermark, as used herein, is a replication of a signature of the physician which is displayed in a low-contrast manner so as to be visible but not obscure the block in which a signature is to be placed. The watermark is preferably the physician's name shown in a cursive font, that is, a typeface that resembles written script.

If the watermark 752 is to be included, it is inserted into the signature block 750, as indicated at block 445. If the watermark is not to be included, then the sample transaction form 700 is presented without it. The form is displayed, as indicated at block 450. Once displayed, the physician can indicate an acceptance by signing on the form using a tablet pen or the like, with the signature in that region or box being captured electronically and stored in the local database, by selecting the "save" button 760, or the physician can refuse the samples and instead select "clear" if the terms of receipt are not acceptable. The watermark provides an encouragement to ensure that the samples are dropped-off with and approved by the authorized customer recipient. Likewise, the watermark provides a deterrent to persons who might otherwise sign on behalf of a physician, yet who are legally unauthorized to accept samples themselves.

The inventory database on the local machine is updated to reflect the quantities received at block 430, either after the acknowledgement at block 435, or after receiving an acceptance of the acceptance form presented at block 450. The update can be synchronized with a central or master inventory to reflect distributions of samples, and, hence, reductions in the allocation of samples remaining in the representative's possession.

As noted above, the inventory management features can forward messages and data from the representative's machine sales information to another location, such as a central computer, a manager's machine, or both. Any communication with the central computer can combine multiple database updates from the local machine, if multiple updates have been made, in a single communication session. A district manager, for example, can monitor sample movement including distributions to authorized physicians, transfers between representatives, any discrepancies resulting from physical audits and other adjustments and returns.

In the foregoing description, certain flow diagrams have been shown and processes described in relation to those flow diagrams which provide a reference for discussion purposes. In an actual implementation of the methods of the present invention, the steps can comprise event-driven routines that can run in parallel and can be launched and executed other than as shown by the simple depiction in the flow diagrams. In short, the particular order of the steps in the flow diagrams is illustrative of the invention, but not limiting of the various permutations that can be achieved in a given embodiment. Accordingly, it is the performance of the steps recited in the claims appended below which is pertinent, and not the order of operation of the steps themselves.

We claim:

1. A method for assisting a representative of a pharmaceutical company in managing the distribution of samples of a product to a customer within a territory of the representative during a site visit to the customer, the samples having been allocated to the representative from an inventory database concerning a central inventory of the pharmaceutical company, comprising the steps of:
   storing inventory information in a database of a machine in a form suitable for differentiating an on-hand quantity from an in-storage quantity;
   presenting within a user interface of the machine a chart or table which distinguishes the on-hand quantity of samples from an in-storage quantity of samples of at least one product;
   receiving from the representative an identification of a product included in the chart or table and a quantity of the product that is for distribution within the territory of the representative to the customer during the site visit;
   updating the database to track at least changes in the on-hand quantity information concerning the product stored in response to the receiving step; and
   communicating the database update to the inventory database at a central machine which differs from the machine,
   wherein the on-hand quantity includes samples with which the representative travels when meeting the customer, and the in-storage quantity includes samples that have been allocated to the representative but with which the representative does not presently travel when meeting the customer, and
   wherein the updating step is performed prior to the communicating step.

2. The method of claim 1, wherein the receiving step includes the steps of:
   selecting the customer from a database included on the machine;
   populating a sample selection table using quantity information stored in the machine for each of one or more products;
   capturing a quantity selection of concerning the one or more products in the populated sample selection table;
   outputting an acceptance form which specifies the quantity selection concerning the one or more products; and
   confirming an acceptance of the acceptance form,
   wherein the receiving step is in response to the confirming step.

3. The method of claim 2, wherein the one or more products in the received quantity selection is associated with a respective lot number, the method including the additional steps of:
   capturing free-hand signature data of the customer in an electronic form, the signature data signifying the distribution of samples to the customer;
   storing as distribution data the distribution of samples in association with each respective lot number;
   searching the stored distribution data for any samples that are subject to recall; and
   communicating a recall message identifying the samples that are subject to recall.

4. The method of claim 3, wherein the searching step further searches the inventory and wherein the communicating step includes communicating the recall message to the representative identifying the samples in the inventory that are subject to recall.

5. The method of claim 1, wherein the on-hand quantity is differentiated on the chart or table from an in-storage quantity for at least two products on the chart or table.

6. The method of claim 1, wherein the storing step comprises separately storing the quantity of on-hand inventory and the quantity of in-storage inventory for at least one product.

7. The method of claim 1, wherein the storing step comprises storing a total quantity and on-hand inventory for each product, wherein the in-storage inventory quantity of a given product comprises a difference between the total quantity and the on-hand inventory.

8. The method of claim 1, wherein the communicating step communicates multiple database updates to the inventory database in one session.

9. The method of claim 1, wherein the product and the quantity identifications are in response to a sample distribution to a customer, or an inventory adjustment, or a return of the sample to a manufacturer of the sample, an inventory transfer step with another representative, or a physical inventory audit.

10. A method for assisting a representative of a pharmaceutical company in managing the distribution of an on-hand quantity of samples of a product to a customer within a territory of the representative during a site visit to the customer, the samples having been received from a central inventory of the pharmaceutical company from an inventory allocated to the representative, comprising the steps of:
    selecting the customer from a database included on a machine;
    populating a sample selection table using quantity information stored in the machine for each of one or more products;

receiving a quantity selection concerning the one or more products in the populated sample selection table that is for distribution within the territory of the representative to the customer during the site visit;

updating the database on the machine so as to reduce the on-hand quantity of samples by the quantity selection concerning the one or more products populated in the sample selection table; and communicating the database update to the central inventory at a central machine which differs from the machine; and outputting an acceptance form having a signature region configured to receive the customer signature, the acceptance form identifying the representative, the selected customer, and the received quantity selection for each of the one or more products and including a watermark comprising the customer name in a cursive font within the signature region, wherein the on-hand quantity includes samples with which the representative travels when meeting the customer, and wherein the updating step is performed prior to the communicating step.

11. The method of claim 10, wherein the populating step sets a non-zero quantity for at least a portion of the one or more products in the sample selection table using the quantity information stored in the machine.

12. The method of claim 11, wherein the quantity information stored in the machine is an on-hand inventory quantity.

13. The method of claim 10, including the additional steps of determining whether the selected customer can be provided particular product samples and presenting the sample chart within a user interface of machine after the determining step, wherein the populating step populates the sample selection table with the particular product samples that can be provided to the customer.

14. The method of claim 13, wherein the determining step includes the steps of comparing data associated with the customer in the machine which relates to sample-receiving history and selectively approving the provision of particular product samples to the customer in response to the comparison.

15. The method of claim 13, wherein the determining step includes the steps of comparing data associated with the customer in the machine which relates to a practice category and selectively approving the provision of particular product samples to the customer in response to the comparison.

16. The method of claim 13, wherein the determining step includes the steps of comparing data associated with the customer in the machine which relates to license status and selectively approving the provision of particular product samples to the customer in response to the comparison.

17. The method of claim 10, wherein the signature region is configured to capture free-hand signature data of the customer in an electronic form.

18. The method of claim 10, wherein the outputting step outputs the acceptance form together with a signature region configured to capture free-hand signature data of the customer in an electronic form.

19. The method of claim 10, including the additional step of updating the database in response to the quantity-receiving step.

20. The method of claim 10, wherein the one or more products in the received quantity selection is associated with a respective lot number, the method including the additional steps of:

capturing free-hand signature data of the customer in an electronic form, the signature data signifying the distribution of samples to the customer;

storing as distribution data the distribution of samples in association with each respective lot number;

searching the stored distribution data for any samples that are subject to recall; and communicating a recall message identifying the samples that are subject to recall.

21. The method of claim 20, wherein the searching step further searches the inventory and wherein the communicating step includes communicating the recall message to the representative identifying the samples in the inventory that are subject to recall.

22. The method of claim 10, including the additional step of updating the database to track at least changes in the on-hand quantity concerning the one or more products stored in response to the receiving step.

* * * * *